United States Patent [19]
Simpson

[11] 3,931,179
[45] Jan. 6, 1976

[54] N,N-BIS(4-QUINAZOLINYL)ALKANEDIAMINES

[75] Inventor: William R. J. Simpson, Mendham, N.J.

[73] Assignee: Sandoz Inc., E. Hanover, N.J.

[22] Filed: Mar. 6, 1974

[21] Appl. No.: 448,524

[52] U.S. Cl. .... 260/256.4 Q; 260/340.6; 260/473.5; 260/561 R; 424/251
[51] Int. Cl.² .................................... C07D 239/86
[58] Field of Search ............................ 260/256.4 Q

[56] References Cited
OTHER PUBLICATIONS

Tietz, "Clinical Chemistry," pp. 153, 807–808.

White et al., "Principles of Biochemistry," 1968, pp. 974–977.

*Primary Examiner*—Donald G. Daus
*Assistant Examiner*—David E. Wheeler
*Attorney, Agent, or Firm*—Gerald D. Sharkin; Richard E. Vila

[57] ABSTRACT

Disclosed are N,N'-Bis(4-Quinazolinyl)alkanediamines, e.g., N,N'-Bis(7-chloro-4-quinazolinyl)-1,9-nonanediamine, having pharmacological activity in animals and useful for example, as anti-obesity agents. Said compounds may be prepared by reacting a 4-haloquinazoline with an alkanediamine.

7 Claims, No Drawings

N,N-BIS(4-QUINAZOLINYL)ALKANEDIAMINES

DISCLOSURE OF INVENTION

The invention relates to chemical compounds which are N,N'-Bis(4-quinazolinyl)alkanediamines having pharmacological activity in animals and to pharmaceutical methods and compositions utilizing the pharmacological properties of said compounds.

The compounds of the present invention may be represented structurally by the following formula (I):

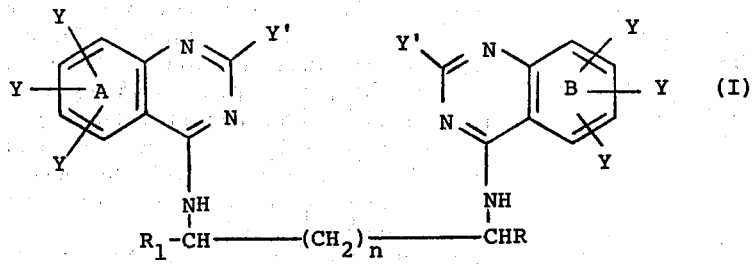

wherein R and $R_1$ are independently hydrogen or alkyl of 1 to 4 carbon atoms, $n$ is 0 to 12, each Y is independently hydrogen, halo of atomic weight of from 18 to 80, i.e. fluoro, chloro or bromo, alkyl of 1 to 4 carbon atoms, alkoxy of 1 to 4 carbon atoms, trifluoromethyl, nitro, amino or N,N-dialkylamino in which each alkyl is of 1 to 3 carbon atoms or two adjacent Y together form 6,7-methylenedioxy or 6,7-ethylenedioxy (with the other Y on each A and B ring so substituted being hydrogen), provided that adjacent Ys do not both have tert-butyl moiety, further provided that no more than 2 Ys in each A and B ring are nitro, trifluoromethyl, amino or dialkylamino, and also provided that when any Y is amino or dialkylamino, then any dissimilar Y is from the group of hydrogen, halo, alkyl and alkoxy, and each Y' is independently hydrogen, halo of atomic weight of from 35 to 80 or alkyl of 1 to 4 carbon atoms, or a pharmaceutically acceptable acid addition salt thereof.

The compounds of the formula (I) may be prepared by reacting a compound of the formula (II):

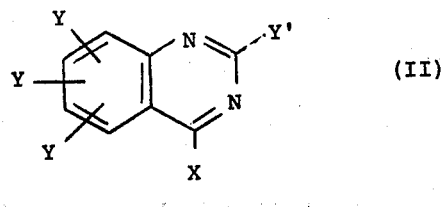

wherein X is chloro or bromo, and

Y and Y' are as above defined with a compound of the formula (III):

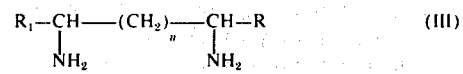

wherein R, $R_1$ and $n$ are as defined.

The preparation of compounds of the formula (I) by reacting a compound of the formula (II) with compound of the formula (III) is preferably carried out in an inert organic solvent in the presence of an acid binding agent. The reaction may be carried out at temperatures in the range of from 10°C. to 160°C., preferably 20°C. to 100°C. The inert organic solvent may be any of several of well-known conventional solvents such as the common aromatic solvents, e.g., benzene and the lower alkanols such as isopropanol and the like. An acid binding agent such as sodium carbonate is preferably employed. The mole ratio of the compound of the formula (II) to the compound of the formula (III) may vary fairly widely with very good results obtained at a ratio of 2:1 or somewhat higher. Two different compounds of the formula (II) in varying ratios to each other and to the compound of the formula (III) may be employed to produce compounds of the formula (I) in which the 2 quinazoline moieties attached to the diaminealkane moiety are different. The preferred compound of the formula I are however, those in which the 2 quinazoline moieties are the same. The reaction product of the formula I may be isolated from the reaction mixture resulting from the above-described preparation by working up by established procedures.

The compounds of the formula I in which one or more Y is amino are preferably prepared by subjecting a compound I in which each Y corresponding to the desired amino group is nitro to reduction in a known manner. For example, the compounds I in which one or more Y is amino may be produced by subjecting a compound I in which one or more of the Y groups are nitro to the action of a suitable elemental metal reducing agent such as iron at elevated temperatures, e.g., 50°C. to 150°C., in an aqueous acidic medium, e.g., hydrochloric acid in an aqueous alcoholic solution. The compounds I in which one or more Y is amino may be also produced by subjecting a compound I in which one or more Y groups are nitro to catalytic hydrogenation in a known manner at 0°C. to 100°C., more usually 10°C. to 50°C., e.g., room temperature, in an aqueous acidic medium, e.g., acetic acid, employing a suitable catalyst, e.g. Raney nickel.

The compounds of the formula III are either known per se or may be produced from known materials by established procedures.

Also within the scope of the compounds of e.g., invention are pharmaceutically acceptable acid addition salts, e., the methane sulfonate, hydronitrate, maleate, fumarate and hydrochloride acid addition salts. The acid addition salts may be readily prepared from the corresponding free bases and vice versa, by conventional procedures. Compound of the formula I and their acid addition salts may also occur in hydrate form and such hydrates are treated as within the definition of compounds I and their salts as the full pharmacological equivalents thereof.

As previously indicated, the compounds of formula I are useful because they possess pharmacological activity in animals. In particular, the compounds are useful as antiobesity agents as indicated by glucose transport tests carried out on male Wistar rats which are dosed orally with 10–150 milligrams per kilogram of body weight of the test compound after at least 20 hours of fasting. One hour after receiving the drug each animal is sacrificed and the upper small intestine is removed and washed with glucose-saline. A 5 cm. section of the intestine is everted so that the mucosal surface is on the outside. One end of the segment is tied off and the center of the sac so formed is filled with oxygen saturated Kreb's biocarbonate buffer. The other end is then closed and the sac is incubated in 10 ml. of oxygen saturated bicarbonate buffer for 60 minutes at 37°C. Both the outside and inside solutions contain initially 0.3% of glucose. At the end of the incubation time, the glucose content of the outer (mucosal) and the inner (serosal) solution is determined using the standard Autoanalyzer procedure. Similar tests are run simultaneously with control animals. The percent inhibition of glucose transport caused by the drug is calculated from the formula:

$$I = 100 - \left(\frac{S_t - M_t}{S_c - M_c}\right) \times 100$$

where $I$ = percent inhibition;
 $S_t$ = glucose concentration (mg.%) of serosal fluid at the end of an experiment in the drug-treated animal;
 $S_c$ = glucose concentration (mg.%) of serosal fluid at the end of an experiment in the control animal;
 $M_t$ = glucose concentration (mg.%) of mucosal fluid at the end of an experiment in the drug-treated animal; and
 $M_c$ = glucose concentration (mg.%) of mucosal fluid at the end of an experiment in the control animal.

The effective dosage of active ingredient employed for the treatment of obesity will vary depending on the particular compound employed and the severity of the condition being treated. However, in general, satisfactory results in the treatment of obesity are obtained when the compounds I are administered at a daily dosage of from about 1.0 milligrams to about 150 milligrams per kilogram of animal body weight, preferably given in divided doses two to four times a day, or in sustained release form. For most large animals in need of either treatment, the total daily dosage is from about 60 to 2000 milligrams. Dosage forms suitable for internal use comprise from about 15 to about 1000 milligrams of the active compound in intimate admixture with a solid or liquid pharmaceutically acceptable carrier or diluent.

For the above uses, the compounds of the formula I are preferably combined with one or more conventional pharmaceutically acceptable carriers, and such other conventional adjuvants as may be desired or necessary, and the resulting composition preferably administered orally in such forms as tablets, capsules, granules, dispersible powders, elixirs, syrups, suspensions and the like. Such compositions may be prepared according to any method known in the art for the manufacture of pharmaceutical compositions. In general, the compositions may be prepared according to any method known in the art for the manufacture of pharmaceutical compositions. In general, the compositions of the invention may contain 1% to 90% by weight of the active ingredient in combination with the inert carrier, more usually 3% to 40%.

The preferred pharmaceutical compositions from the standpoint of preparation and ease of administration are solid compositions, particularly hard-filled capsules and tablets.

Tablets and capsules containing the ingredients indicated below may be prepared by conventional techniques and are useful in treating obesity at a dose of one tablet or capsule 2 to 4 times a day.

| Ingredients | Weight Tablet | Capsule |
|---|---|---|
| N,N'-Bis(7-chloro-4-quinazolinyl)-1,9-nonanediamine | 50 | 50 |
| Tragacanth | 10 | — |
| Lactose | 197.5 | 250 |
| Corn starch | 25 | |
| Talcum | 15 | |
| Magnesium stearate | 2.5 | |

The following pharmaceutical composition is formulated with the indicated amount of active agent using conventional techniques. The oral liquid suspension represents formulations useful as unit doses and may be administered in the treatment of obesity.

| Ingredients | oral liquid suspension(mg.) |
|---|---|
| N,N'-Bis(7-chloro-4-quinazolinyl)-1,9-nonanediamine | 50 (or less) |
| sodium carboxy methyl cellulose U.S.P. | 12.5 |
| magnesium aluminum silicate | 47.5 |
| flavor | q.s. |
| color | q.s. |
| methyl paraben, U.S.P. | 4.5 |
| propyl paraben, U.S.P. | 1.0 |
| polysorbate 80 (e.g. Tween 80), U.S.P. | 5 |
| sorbitol solution, 70% U.S.P. | 2,500 |
| buffer agent to adjust pH for desired stability | q.s. |
| water | q.s. to 5 ml. |

The compounds of the formula II employed in the preparation of the compounds of the formula I are either known per se or may be prepared from known materials by known procedures. The 4-halo-6,7-ethylenedioxyquinazolines are preferably prepared according to the following reaction scheme:

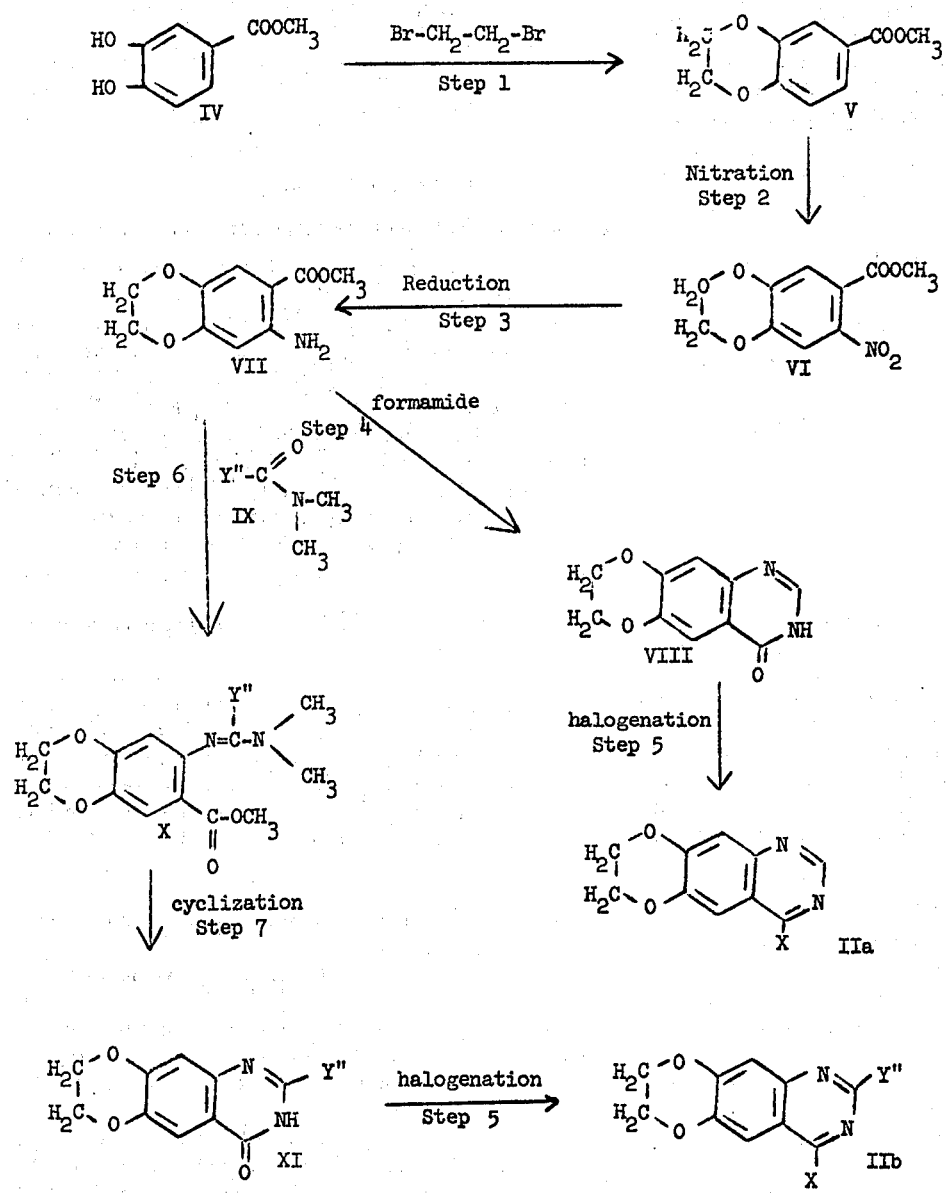

In the above reaction scheme X is as previously defined and Y″ is alkyl of 1 to 4 carbon atoms.

The reaction of Step 1 involves reacting the compound of the formula IV with 1,2-dibromoethane in the presence of a strong base which is preferably an alkali metal alkoxide, more preferably sodium methoxide. An excess of the 1,2-dibromoethane is usually employed and may be used as the solvent for the reaction. However, an inert conventional solvent such as an alcohol, e.g. methanol, is preferably employed. The reaction may be carried out at temperatures of from 20°C. to 120°C., preferably 40°C. to 80°C.

Step 2 is a conventional aromatic nitration involving the reaction of the compound V with nitric acid in the presence of acetic acid at a temperature of from 20°C. to 100°C., more usually 40°C. to 80°C.

Step 3 is a conventional reduction of an aromatic nitro group preferably effected by hydrogenation employing a 5–10% palladium on charcoal catalyst. Glacial acetic acid is a preferred solvent for the reduction which may be carried out at temperatures of from 0°C. to 60°C., preferably 10°C. to 40°C.

Step 4 involves cyclizing the compound VII with formamide which may be employed in excess as the solvent. The reaction may be carried out at temperatures of from 100°C. to 220°C., preferably 150°C. to 215°C., and conveniently at reflux.

Step 5 is a conventional halogenation of cyclic keto group preferably carried out employing a phosphorus oxyhalide is preferably employed in excess as the solvent for the reaction which is conveniently effected at the reflux temperature of the system. The reaction may be carried out under an inert atmosphere, e.g., nitrogen, but such conditions are not necessary.

Step 6 involving the reaction of compound VII with a compound of the formula IX is conveniently carried out in an inert atmosphere at temperatures of from 10°C. to 100°C., preferably 30°C. to 60°C., and in the presence of a phosphorus oxyhalide, preferably phosphorus oxychloride. Alternately and preferably, the compound IX is first reacted with the phosphorus oxyhalide at 10°C. to 100°C. and the resulting reaction product then reacted with the compound VII.

Step 7 involves the cyclization of a compound X employing ammonia in the presence of ammonium chloride. The reaction is conveniently conducted at temperatures of from 50°C. to 150°C. in a sealed bomb employing excess ammonia as the liquid reaction medium.

In the reaction of Steps 1-7, inclusive, the desired reaction product may be recovered by working up by conventional procedures.

The following examples are given for the purpose of illustration only.

EXAMPLE 1

N,N'-bis(7-chloro-4-quinazolinyl)-1,9-nonanediamine

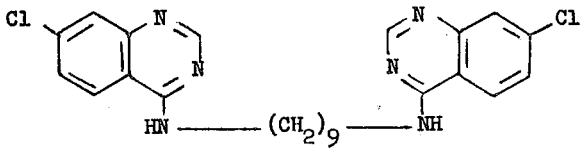

A mixture of 1.99 g. of 4,7-dichloroquinazoline, 0.79 g. of 1,9-diaminononane, 2.5 g. of sodium carbonate and 25 ml. of isopropanol is stirred at room temperature for 2 hours. The reaction mixture is then diluted with 100 ml. of chloroform, filtered and concentrated in vacuo. The solid residue is crystallized from ethanol to obtain N,N'-bis(7-chloro-4-quinazolinyl)-1,9-nonanediamine, m.p. 190°–192°C. which is readily converted into dimethanesulfonate acid addition salt form which melts at 159°–162°C. on crystallization from ethanol/ether.

EXAMPLE 2

Following the procedure of Example 1, the following additional compounds of the invention are prepared:
A. N,N'-Bis(7-trifluoromethyl-4-quinazolinyl)-1,9-nonanediamine dimethanesulfonate, m.p. 134°–140°C.
B. N,N'-Bis(6,8-dichloro-4-quinazolinyl)-1,9-nonanediamine, m.p. 214.5°–215.5°C.
C. N,N'-Bis(6-nitro-4-quinazolinyl)-1,9-nonanediamine, m.p. 140°C.
D. N,N'-Bis(6-chloro-4-quinazolinyl)-1,9-nonanediamine, m.p. 165°–169°C.
E. N,N'-Bis(6,7-methylenedioxy-4-quinazolinyl)-1,9-nonanediamine.
F. N,N'-Bis(7-chloro-4-quinazolinyl)-1,10-decanediamine, m.p. 179°C.
G. N,N'-Bis(6-chloro-4-quinazolinyl)-1,10-decanediamine dimethanesulfonate, m.p. 196°–199°C.
H. N,N-Bis(7-trifluoromethyl-4-quinazolinyl)-1,10-decanediamine dimethanesulfonate, m.p. 198°–204°C.
I. N,N'-Bis(7,8-dimethyl-4-quinazolinyl)-1,10-decanediamine, m.p. 194°C.
J. N,N'-Bis(6,8-dichloro-4-quinazolinyl)-1,10-decanediamine, m.p. 188°–192°C.
K. N,N'-Bis(6,7-dimethyl-4-quinazolinyl)-1,12-dodecanediamine, m.p. 175°C.
L. N,N'-Bis(7-nitro-4-quinazolinyl)-1,12-dodecanediamine, m.p. 202°C.
M. N,N'-Bis(7,8-dimethyl-4-quinazolinyl)-1,12-dodecanediamine, m.p. 169°C.
N. N,N'-Bis(7-chloro-4-quinazolinyl)-1,2-ethanediamine.
O. N,N'-Bis(7-chloro-4-quinazolinyl)-1,6-hexanediamine.
P. N,N-Bis(6-nitro-4-quinazolinyl)-1,6-hexanediamine.
Q. N,N-Bis(6,7-ethylenedioxy-4-quinazolinyl)-1,9-nonanediamine.

EXAMPLE 3

4-Chloro-6,7-ethylenedioxyquinazoline

Step A: Preparation of 3,4-ethylenedioxybenzoic acid methyl ester

A solution of 4.20 g. of 3,4-dihydroxybenzoic acid methyl ester in 10.0 ml. of methanol is combined with 7.0 g. of sodium methoxide and then 15.0 g. of 1,2-dibromoethane is added. The resulting mixture is refluxed under nitrogen for 24 hours, then cooled, filtered, evaporated in vacuo and the resulting oil dissolved in 50 ml. of chloroform. The resulting solution after again filtering is chromatographed over 100 ml. of silica gel eluting with chloroform to obtain 3,4-ethylenedioxybenzoic acid methyl ester, m.p. 43°–45°C.

Step B: Preparation of 6-nitro-3,4-ethylenedioxybenzoic acid methyl ester

To a solution of 5.0 g. of 3,4-ethylenedioxybenzoic acid methyl ester in 5.0 mls. of glacial acetic acid is added dropwise 5.0 mls. of 70% nitric acid at 50°–60°C. After addition the reaction mixture is kept at 55°C. for one hour, then cooled and 50 mls. of ice water added. The resulting precipitate is recovered by filtering, water washed and dried to obtain 6-nitro-3,4-ethylenedioxybenzoic acid methyl ester, m.p. 115°–118°C.

Step C: Preparation of 6-amino-3,4-ethylenedioxybenzoic acid methyl ester

A mixture of 6.0 g. of 6-nitro-3,4-ethylenedioxybenzoic acid methyl ester, 150 mg. of 5% palladium on charcoal and 20 mls. of glacial acetic acid is hydrogenated under an initial hydrogen pressure of 30–40 p.s.i. and without external heating. After four hours, the reaction mixture is filtered diluted with 80 ml. of ice water, stirred for up to one half hour and the resulting precipitate filtered off, water washed and dried to obtain 6-amino-3,4-ethylenedioxybenzoic acid methyl ester, m.p. 73°–77°C.

Step D: Preparation of 6,7-ethylenedioxyquinazolin-4(3H)-one

A mixture of 2.0 g. of 6-amino-3,4-ethylenedioxybenzoic acid methyl ester and 6 ml. of 99% formamide is refluxed for 1.5 hours, then cooled, diluted with 5 ml. of water and the resulting precipitate filtered off, water washed and dried to obtain 6,7-ethylenedioxyquinazolin-4(3H)-one, m.p. 275°C.

Step E: Preparation of 4-chloro-6,7-ethylenedioxyquinazoline

A mixture of 25.3 g. of 6,7-ethylenedioxyquinazolin-4(3H)-one and 50 ml. of phosphorus oxychloride is refluxed for 10 minutes, cooled, and added with stirring to one liter of ice. After addition of concentrated ammonia the resulting mixture is extracted with chloroform and the chloroform solution chromatographed through 300 mls. of silica gel while eluting with chloroform. Evaporation of the eluent yields 4-chloro-6,7-ethylenedioxyquinazoline, m.p. 169°–174°C.

EXAMPLE 4

2-Methyl-4-chloro-6,7-ethylenedioxyquinazoline

Step A: Preparation of 2-(α-dimethylaminoethylideneamino)-4,5-ethylenedioxybenzoic acid methyl acid To a mixture prepared by mixing 15.2 g. of N,N-dimethylacetamide and 40 ml. of phosphorus oxychloride is added portionwise 35.0 g. of 6-amino-3,4-ethylenedioxybenzoic acid methyl ester while maintaining 40°–45°C. The reaction mixture is stirred for 4 hours at 40°–60°C. the reaction mixture is added to ice, treated with concentrated ammonia, extracted with chloroform and the chloroform solution evaporated to obtain an oil of 2-(α-dimethylaminoethylideneamino)-4,5-ethylenedioxybenzoic acid methyl acid.

Step B: Preparation of 2-methyl-6,7-ethylenedioxyquinazolin-4(3H)-one

A mixture of 12 g. 2-(α-dimethylaminoethylideneamido)-4,5-ethylenedioxybenzoic acid methyl acid, 12 g. of ammonium chloride and 100 ml. of liquid ammonia is contained in a sealed bomb and heated at 110°C. for 10 hours. The ammonia is evaporated off and the resulting solids washed several times with water and dried to yield 2-methyl-6,7-ethylenedioxyquinazolin-4(3H)-one, m.p. 275°C.

Step C: Preparation of 2-methyl-4-chloro-6,7-ethylenedioxyquinazoline

Following essentially the procedure of Step E of Example 3 there is obtained 2-methyl-4-chloro-6,7-ethylenedioxyquinazoline, m.p. 168.5°–169.5°C.

EXAMPLE 5

Following the procedure of Example 1, the following additional compounds of the invention are prepared:

A. N,N'-Bis(2-methyl-6,7-ethylenedioxy-4-quinazolinyl)-1,9-nonanediamine.
B. N,N'-Bis(6,7-dimethyl-4-quinazolinyl)-1,9-nonanediamine dimethanesulfonate, m.p. 96°C.
C. N,N'-Bis(6,7-dimethyl-4-quinazolinyl)-1,10-decanediamine dimethanesulfonate, m.p. 110°C.
D. N,N'-Bis(6,7-dimethyl-4-quinazolinyl)-1,8-octanediamine dimethanesulfonate, m.p. 236°–239°C.
E. N,N'-Bis(6,7-dimethoxy-4-quinazolinyl)-1,2-ethanediamine dimethanesulfonate, m.p. 282°–285°C. (decomp.).
F. N,N'-Bis(6-dimethylamino-4-quinazolinyl)-1,9-nonanediamine dimethanesulfonate.
G. N,N'-Bis(6,7-dimethoxy-4-quinazolinyl)-1,3-propanediamine dimethanesulfonate, m.p. 159°C. and 172°–174°C. (decomp.).
H. N,N'-Bis(6,7,8-trimethoxy-4-quinazolinyl)-1,2-ethanediamine dimethanesulfonate, m.p. 252°–253.3°C.
I. N,N'-Bis(6,7,8-trimethoxy-4-quinazolinyl)-1,3-propanediamine dimethanesulfonate, m.p. 250°–252°C. (decomp.).

What is claimed is:
1. A compound of the formula:

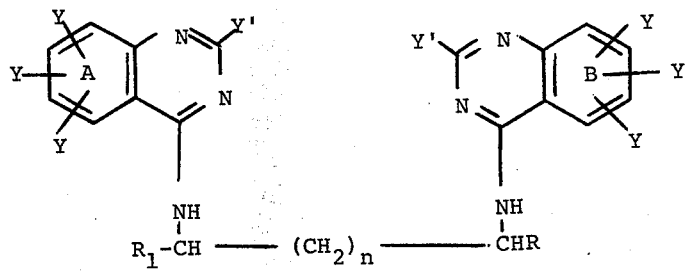

wherein R and $R_1$ are independently hydrogen or alkyl of 1 to 4 carbon atoms, $n$ is 0 to 12, each Y is independently hydrogen, fluoro, chloro, bromo, alkyl of 1 to 4 carbon atoms, alkoxy of 1 to 4 carbon atoms, trifluoromethyl, nitro, amino or N,N-dialkylamino in which each alkyl is of 1 to 3 carbon atoms or two adjacent Y together form 6,7-methylenedioxy or 6,7-ethylenedioxy with the other Y on any such alkylenedioxy substituted ring being hydrogen, provided that adjacent Ys do not both have a tert-butyl moiety, further provided that no more than 2 Ys in each A and B ring are nitro, trifluoromethyl, amino or dialkylamino, and also provided that when any Y is amino or dialkylamino, then any dissimilar Y is hydrogen, fluoro, chloro, bromo, alkyl or alkoxy, and each Y' is independently hydrogen, fluoro, chloro, bromo or alkyl of 1 to 4 carbon atoms, or a pharmaceutically acceptable acid addition salt thereof.

2. A compound of claim 1 in which $n$ is 6 to 10.

3. A compound of claim 2 in which each of R and $R_1$ is hydrogen.

4. The compound of claim 3 which is N,N'-Bis(7-chloro-4-quinazolinyl)-1,9-nonanediamine.

5. The compound of claim 3 which is N,N'-Bis(7-trifluoromethyl-4-quinazolinyl)-1,9-nonanediamine.

6. The compound of claim 3 which is N,N'-Bis(6,8-dichloro-4-quinazolinyl)-1,9-nonanediamine.

7. A compound of claim 1 in which $n$ is 7.

* * * * *